United States Patent
Crouch et al.

(10) Patent No.: US 6,951,723 B2
(45) Date of Patent: Oct. 4, 2005

(54) ASSAY OF MICRO-ORGANISMS IN CELL CULTURES

(75) Inventors: Sharon Patricia Mary Crouch, Nottingham (GB); Dawn Ann Bradbury, Nottingham (GB); Kevin John Slater, Nottingham (GB)

(73) Assignee: Lumitech (UK) Limited, City Link ( * ) Notice: Subject to any disclaimer, the term of this patent is extended or adjusted under 35 U.S.C. 154(b) by 397 days.

(21) Appl. No.: 10/139,740

(22) Filed: May 7, 2002

(65) Prior Publication Data

US 2003/0049708 A1 Mar. 13, 2003

Related U.S. Application Data

(63) Continuation of application No. PCT/GB00/04264, filed on Nov. 8, 2000.

(30) Foreign Application Priority Data

Nov. 8, 1999 (EP) .............................................. 99308856
Nov. 8, 1999 (GB) .............................................. 9926420

(51) Int. Cl.⁷ ............................ C12Q 1/68; C12Q 1/70; C12M 3/00

(52) U.S. Cl. .............................. 435/6; 435/5; 435/288.7

(58) Field of Search .............................. 435/6, 5, 288.7, 435/4

(56) References Cited

FOREIGN PATENT DOCUMENTS

GB 2323167 9/1998 .......... G01N/21/78

OTHER PUBLICATIONS

Written Opinion mailed Aug. 24, 2001 in PCT/GB/00/04264.

*Primary Examiner*—Gary Benzion
*Assistant Examiner*—Joyce Tung
(74) *Attorney, Agent, or Firm*—Banner & Witcoff, Ltd.

(57) ABSTRACT

Micro-organisms which over-produce ATPase, especially mycoplasmas in a sample of a cell culture, are detected by making use of the ATPase activity to convert cellular or externally added ATP to ADP. The decrease in ATP externally added or the increase or absolute level of ADP produced from cellular ATP can then be detected or measured. For example, if a reagent such as phosphenol pyruvate/pyruvate kinase is added to convert that ADP back to ATP, the resulting high level of ATP can be detected bioluminescently using the reaction: Luciferin+luciferase enzyme+ATP→hv+products.

25 Claims, 4 Drawing Sheets

ASSAY OF MICRO-ORGANISMS IN CELL CULTURES

BACKGROUND OF THE INVENTION

1. Field of the Invention

The present invention relates to a method of assay of micro-organisms, especially small wall-less bacteria such as mycoplasmas, in cell cultures.

2. Description of the Related Art

Mycoplasma are a large and widespread group of prokaryotes. They are essentially bacteria with the smallest known genomes and are found amongst members of mollicutes. This class presently comprises six eubacterial genera Acholeplasma, Anaeroplasma, Asteroplasma, Mycoplasma, Spiroplasma and Ureaplasma.

The Mycoplasmas and Ureaplasmas are parasites in different vertebrates, from which they obtain their essential compounds such as fatty acids, amino acids, precursors for nucleic acid synthesis and cholesterol. Only Acholeplasma and Asteroplasma do not require cholesterol for growth.

These flexible, pleomorphic organisms can be as small as 200–300 nm in diameter and can achieve very high densities in cell cultures, ($10^7$–$10^8$ organisms/mL), without discernible pH changes or turbidity. Contamination rates are even higher for cell lines routinely grown in antibiotic-containing medium. There are currently more than 120 species in six genera, many of which are pathogenic. The vast majority of cell culture contaminants belong to only 6 species of human, bovine or porcine origin, namely *Mycoplasma hyorhinis, Mycoplasma arginini, Mycoplasma salivarium, Mycoplasma orale, Mycoplasma fermentans* and *Acholeplasma laidlawii*.

Surveys and research studies have repeatedly shown that 15–50% or more of all cell lines are contaminated by mycoplasmas. They alter virtually every property and parameter measured in cell cultures, including hybridoma selection rates, protein and nucleic acid synthesis, immunogenicity, chromosomal breakage and production of virus and proteins such as interferons and monoclonal antibodies. As a result of this widespread problem, research and production of biological materials is often unknowingly done using mycoplasmal contaminated cell cultures. Thus, the validity and significance of research and the safety of the biologicals produced from contaminated cell cultures are jeopardised.

Because of their small size and lack of cell wall, mycoplasmas often pass through the 450 or even 200 nm filters used to "sterilise" cell culture media and sera, resulting in low levels of these organisms being accidentally introduced into cultures during routine feeding.

Tests for detecting mycoplasmas fall into two basic categories: direct culture with media; or indirect tests measuring specific biochemical markers or other characteristics associated with mycoplasmas.

Direct culture requires the use of one or more complex nutritionally enriched media and carefully controlled environmental conditions. Even then, some mycoplasmal strains are difficult to grow in culture without cells. Properly done, with appropriate positive and negative controls, direct culture testing offers the greatest security, but is rather slow, usually requiring up to 28 days for completion.

Indirect tests include DNA fluorochrome staining, DNA probes, PCR, ELISA, autoradiography, immunofluorescence and specific biochemical assays. While faster than direct culture methods, usually taking only 1–5 days to complete, indirect tests are not yet as sensitive and usually require higher levels of contamination (e.g. $10^4$ or more organisms/mL) for detection.

The PCR-based kit of Stratagene is widely used, but is expensive, additional PCR chemicals are required and the running of PCRs requires technical expertise not always conveniently available. Also, competition between the internal control template DNA and the mycoplasma DNA frequently results in the control not being visible on the gel when the sample is contaminated with mycoplasma.

It is a problem to find an alternative rapid, indirect method which does not require PCR skills.

SUMMARY OF THE INVENTION

The present invention is based on a discovery that many small microorganisms, including notably mycoplasmas, over-produce the enzyme ATPase, in such large amounts that it is possible to use this phenomenon as the basis of an assay for the micro-organisms. The ATPase activity of these micro-organisms converts sufficient cellular or externally added adenosine triphosphate (ATP) to adenosine diphosphate (ADP) to make the ADP detectable. All common species of the genus Mycoplasma as well as wall-less bacteria of the genera Acholeplasma, Ureaplasma and Spiroplasma, and other extracellular and intracellular parasites, such as those of the genus *Chlamydia*, are believed to over-produce ATPase. The present inventors have found that this can form the basis of a method of assay of these micro-organisms.

In one aspect, the invention provides a method of assay of ATPase-producing micro-organisms in a sample suspected of contamination or infection by them, which comprises establishing conditions effective to cause the ATPase produced by said micro-organisms and ATP to produce ADP and determining the occurrence or extent of the reaction.

A preferred method of assay involves making use of the bioluminescent reaction:

luciferin+luciferase+ATP→hv (light)+products or any similar reaction, e.g. using a derivative of luciferin. The term "luciferase" means any enzyme which reacts with luciferin or a derivative thereof, in the presence of ATP, to give a light output (luminescence).

In one aspect of the invention, ATP is added to the sample and caused to react with the ATPase, whereby loss of the exogenous ATP, consumed in the reaction, is assayed.

In another aspect of the invention, the ATPase is allowed to react with ATP present in the sample, e.g. endogenous ATP within biological cells present in the sample, to produce ADP, which is then re-converted to ATP, which takes part in the bioluminescent reaction.

The term "assay" herein includes qualitative assessment, semi-quantitative measurement or assessment and quantitative measurement.

The terms "bioluminescent reagent", "ADP-converting agent" and "ATP releasing agent" or equivalent include the plural, whenever the context permits, i.e each may have one or more components.

DESCRIPTION OF THE PREFERRED EMBODIMENTS

For convenience, the following description refers primarily to mycoplasmas, referring to a sub-class of micro-organisms which includes the genera Mycoplasma, Acholeplasma and Ureaplasma. However, it applies equally to other microorganisms which produce ATPase in large amounts and should be read accordingly.

The invention applies particularly to a sample of biological cells, an extract therefrom or a lysate thereof. Most especially it applies to cell cultures. These are normally cultures grown for research purposes in the laboratory. These include cell lines developed for screening drugs, hybridomas etc. However, also included are cells grown in a hospital laboratory which have been deliberately infected with the body fluid of a patient suspected of containing ATPase-producing micro-organisms associated with an illness. Such cells may be infected with body fluid, e.g. sputum or a lavage, from the patients, especially a bronchoalveolar lavage from patients suffering from *Mycoplasma pneumoniae* infections.

The increase in ADP present in a cell culture results from the ATPase action of the mycoplasma on ATP present in the cultured cells or associated with the cells, for example around the outside of the cell wall, producing ADP. The cells are then treated to release their ADP. The ADP is converted to ATP, e.g. by adding another enzyme-based reagent. Measurement of ATP, after conversion from ADP, can make use of any light-emitting reaction in which the level of light output (its intensity) is related to the amount of ATP present in the sample. A particularly preferred such reaction is the bioluminescent reaction between luciferin, or a derivative thereof, a luciferase and ATP as described above. Alternatively, the ATP can be measured calorimetrically.

In one aspect of the invention, ADP is detected or measured. Theoretically, one would measure ATP released from the cells along with the ADP, and then, after converting the ADP to ATP, measure a higher level of ATP and use the difference to determine the level of ADP. Indeed, this is also one practical way of carrying out the invention. For example, an initial reading is taken, just before, simultaneously with or just after the ADP converting agent is added. Conveniently, an "ATP monitoring reagent", comprising luciferin and luciferase, is reconstituted from a frozen state with nucleotide releasing reagent", i.e. ADP-converting reagent and this mixture is added directly to the sample. The level of luminescence is read immediately. This represents the initial concentration of ATP. A concentration of ADP+ATP is measured after, say, 5 minutes when the level of luminescence has reached a plateau. Alternatively, a reading can be taken when the reaction has proceeded to completion. Where concentrations of ADP and ATP are determined, the measurements can be used in any mathematical way to determine the contaminated or infected condition of the sample. They are preferably expressed as a ratio of ADP to ATP and the contaminated status of the cells of the sample can be determined based either on a predetermined value of this ADP to ATP ratio for the particular cell type under investigation or by numerical ranges which apply to most types of cell likely to be encountered in the samples.

However, in practice, it is usually found that the level of ATP after conversion of the ADP is so high that there is no need to take any readings of the luminescence at around the time that the converting agent is added. Measuring or (in many cases) merely visualising the intensity of luminescence after the conversion is enough.

All readings of chemiluminescence are typically taken over a time period of about a second and integrated over that period.

Thore, *Science Tools*, 26, 30–34 (1979), teaches that the initial rapid light emission phase of the luciferase reaction is the most reliable measure of ATP concentration. Conventional bioluminescent assay techniques therefore require measurements to be taken as soon as possible after the addition of luciferase and luciferin, before any signal decay occurs. This is preferably done in the present invention.

Alternatively, advantage can be taken of the fact that the light emission does not fade entirely, but eventually reaches a substantially constant condition. At this low and substantially constant ATP level, it becomes easy to measure ADP, by adding to the bioluminescent reaction reagent(s) which convert ADP to ATP and taking measurements of light intensity thereafter, see GB Pat. No 2,323,167 B (BTG International Limited). The assay of that patent is to determine the physical condition of a sample of biological cells in vitro, especially to determine whether they are exhibiting apoptosis. In this embodiment of the present invention, the ADP converting reagent is typically added after a time of 5–12 minutes, preferably 8–11 minutes, after the beginning of the luminescent reaction. The ATP level is read at that time.

In another aspect of the invention, the ATPase produced, either present in the sample as taken or released from the cells by extraction or lysis, is measured more directly. In this embodiment, the ATPase is reacted with a pre-determined amount of ATP and the loss in ATP consumed in the reaction thereof with ATPhase, is detected or measured. Alternatively, the gain in ADP or the total amount of ATP+ADP generated can be detected or measured. Again, ADP is conveniently measured by conversion to ATP and the ATP is conveniently measured bioluminescently, as described above.

We have found that for screening of mycoplasma contamination in cultures, the ADP reading can be determined very soon after the measurement of the ATP. For example in the assays of GB 2,323,167B there is a requirement for a decay of the light output after addition of the ATP monitoring reagent, in order to detect the low levels of ADP that can be present in an apoptotic culture. However, the effect of mycoplasma contamination (even at very low level of contamination) is to produce so much ADP within an otherwise healthy population of cells, that it can be detected in the presence of high ATP concentrations. There is therefore no need for the decay of the original ATP signal. The assays of the invention can therefore be performed in a variety of ways.

1. In one embodiment, a protocol laid out in GB 2,323, 167B can be used (as shown schematically in FIG. 1A). The ATP monitoring reagent is added to the culture and a 1–10 sec integral reading taken when the resulting bioluminescence signal reached a peak. This first reading ('A') corresponds to the ATP concentration in the culture. Following a delay for reduction of the light signal, such as 10 minutes, the ADP converting reagent is added and immediate measure of light output (1–10 seconds) obtained corresponding to the baseline value for ADP measurement (ADP0 or 'B').

Figure 1A:
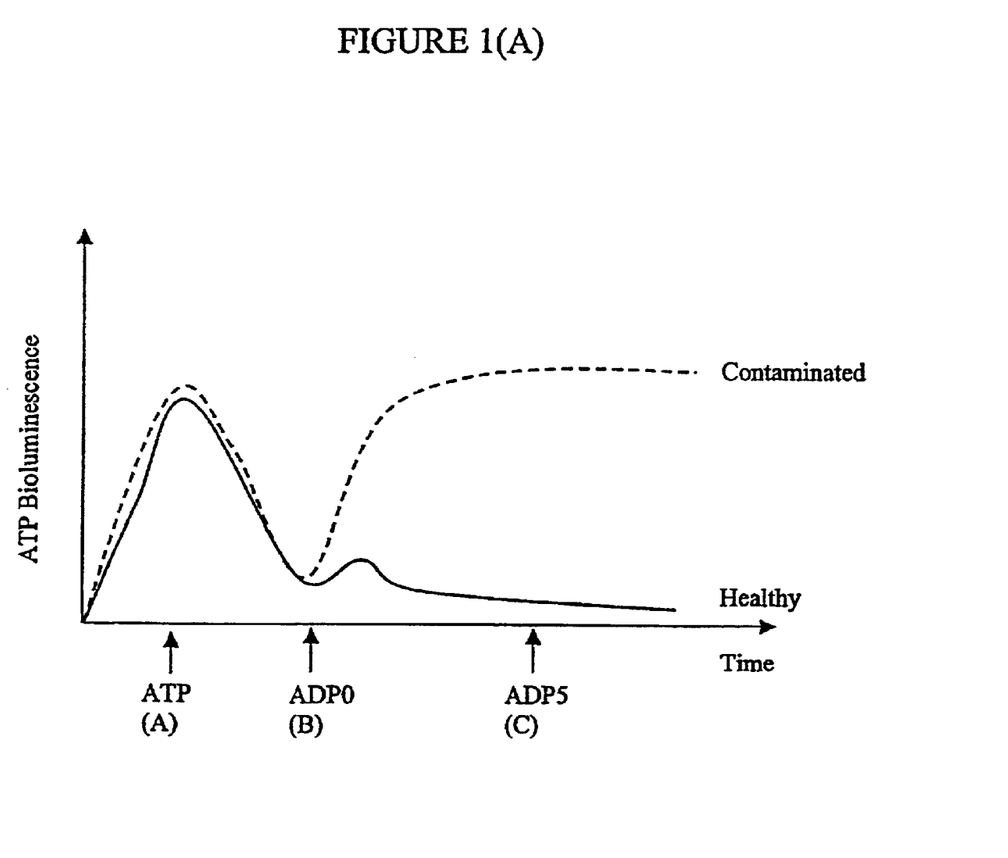
FIG. 1 shows a schematic diagram of the determination of ADP:ATP ratios in healthy (A) and mycoplasma-contaminated (B) cell cultures.
Figure 1B:
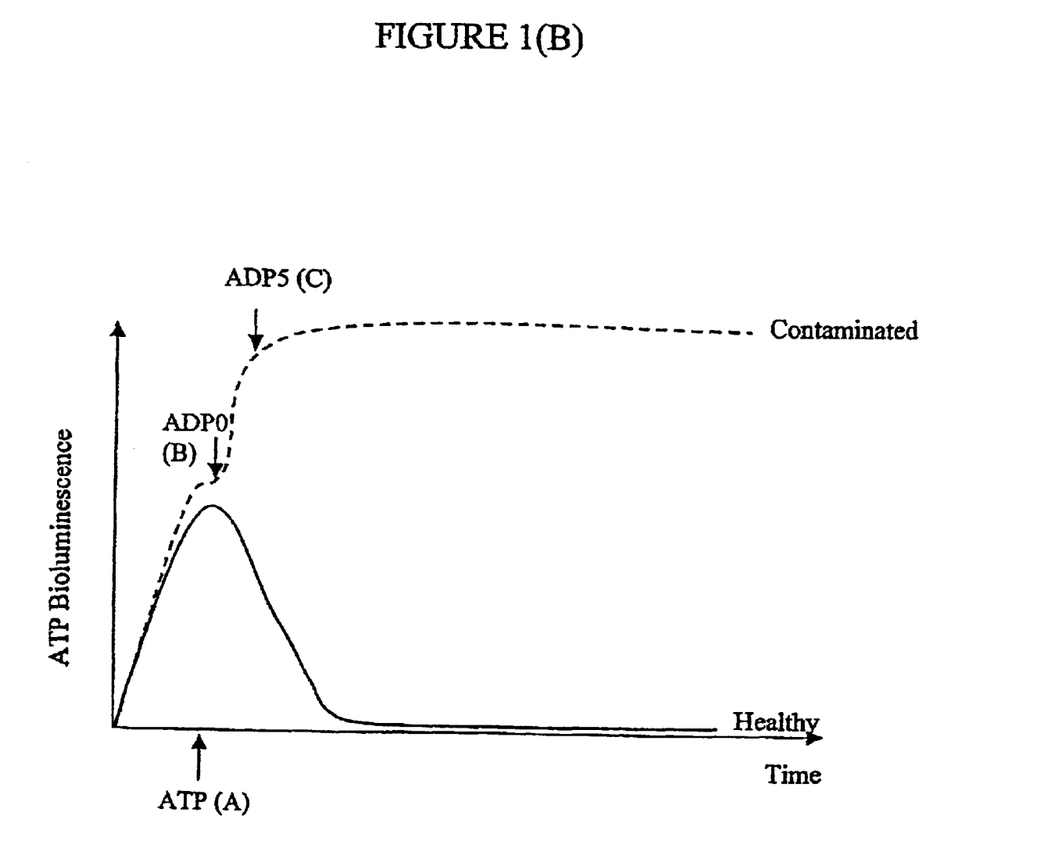

A final bioluminescence reading (ADP5 or 'C') is then taken after a further delay of, for example, 5 minutes, i.e. after any ADP present in the culture has been converted to ATP. The final reading minus the second reading (i.e. C-B) gives a measure of ADP concentration in the culture. Hence, an ADP:ATP ratio for the culture can be expressed as (C-B)/A.

As is evident from FIG. 1(A), the addition of the converting reagent to the culture of healthy cells produces only small increase in light signal, due to the low level of ADP present in such cells. The final 'C' reading may be read either at the height of this secondary (or ADP) peak or, alternatively, may be read after the light signal has decayed again. Indeed, in some cases the levels of ADP in healthy cells may be so low that increase in light signal due to the conversion of ADP to ATP is completely masked by the decaying ATP light signal. In such circumstances, an secondary (ADP) peak will not be observed.

It will be appreciated that where the 'C' reading is taken at the height of the ADP peak, the C-B value gives a 'true' measure of ADP. However, where no ADP peak is observed or where the 'C' reading is taken after the decay of the ADP peak, then the C-B value does not give a 'true' measure of ADP. Indeed, the C-B value may be negative, leading to a negative ratio of ADP:ATP.

In contrast, ADP levels are very high in mycoplasma-contaminated cultures, hence the C-B calculation gives a large (and positive) value, which corresponds to the amount of ADP present in the cell culture, leading to a large and positive ADP:ATP ratio.

In another embodiment, the procedure is the same as described above except that there is no requirement to wait 10 minutes for the reduction (i.e. decay) of the initial ATP light signal ('A'). Thus, the 'A' and 'B' readings are essentially the same. In healthy cells, there is typically little or no ADP to convert to ATP following addition of the ADP converting reagent, hence the bioluminescence signal is seen simply to decay (any increase in signal due to the conversion of ADP to ATP being masked by the decaying ATP signal, as described above). Consequently, the C-B value is large and negative, leading to a large and negative ADP:ATP ratio for such cells.

However, in the presence of the high levels of ADP associated with mycoplasma contamination, the conversion reaction results in a marked and rapid rise in bioluminescence, which can be detected much earlier than 5 minute delay typically needed prior to measuring reading 'C' (in fact, the bioluminescence signal will increase in a linear fashion for as long as 60–120 minutes in contaminated cells). In this case, the C-B value is large and positive, leading to a large and positive ADP:ATP ratio for such cells. The positive versus negative ratio in contaminated and healthy cells, respectively, provides a convenient and easy screening test for mycoplasma contamination of a culture.

Figure 2:
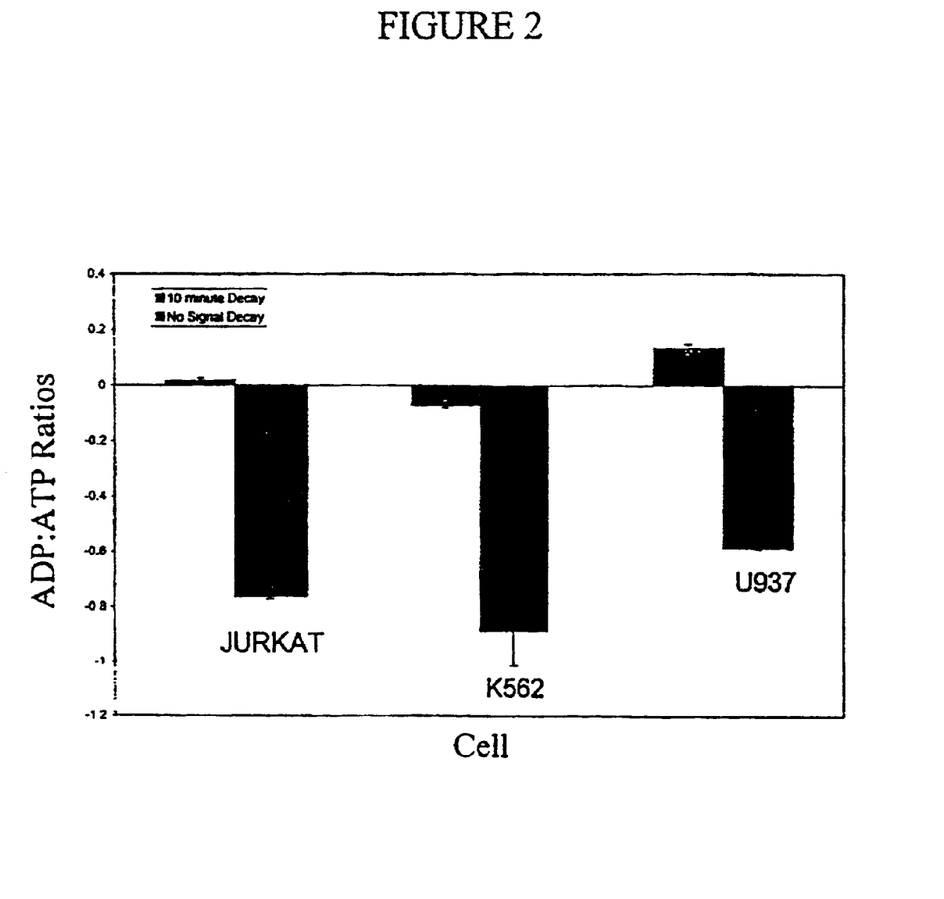
FIG. 2 shows a comparison of ADP:ATP ratios in three different healthy cell types generated using two a protocol with and without a 10 minute delay between measuring ATP concentration (reading 'A') and baseline ADP (reading 'B'). Data are expressed as the mean of three separate experiment±SD.
Figure 3:
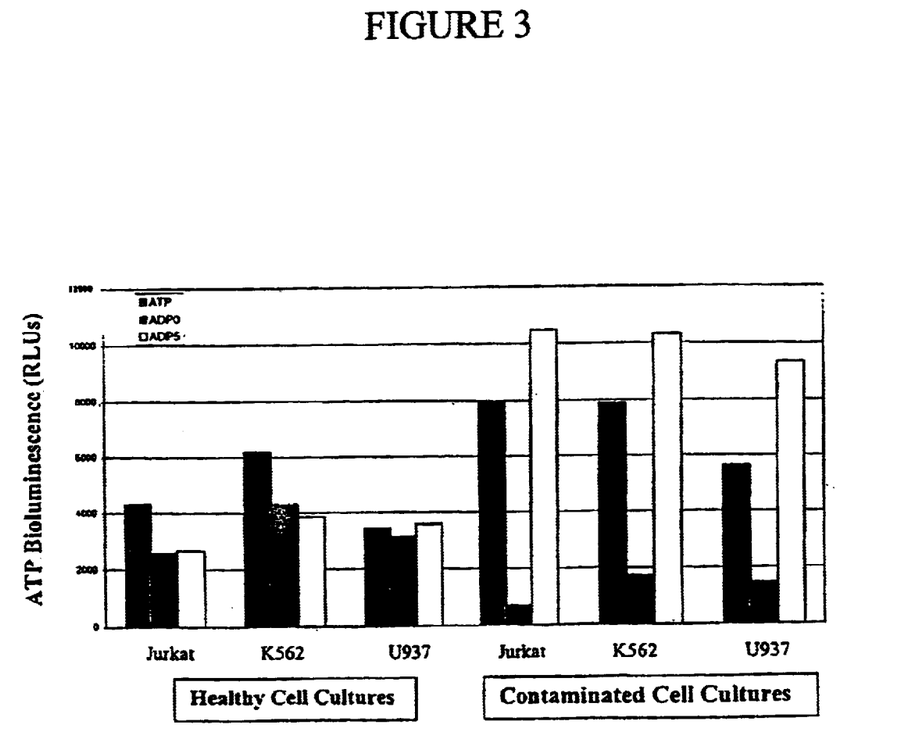
FIG. 3 shows exemplary bioluminescence readings at time points 'A' (ATP) 'B' (ADP0) and 'C' (ADP5) obtained for healthy and mycoplasma-contaminated cultures of three different cell types. The protocol incorporated a 10-minute delay between taken reading 'A' and reading 'B'. Data are from one representative experiment performed in triplicate.

FIG. 2 shows a comparison of the ADP:ATP ratios obtained in healthy cells using embodiments 1 and 2 described above. Exemplary bioluminescence readings at time points A, B and C for healthy and contaminated cells, obtained using protocols 1 and 2 described above, are shown in FIG. 3.

3. In the absence of an instrument with injectors, the assay of the invention can be performed manually, e.g. by manual pipetting. The ATP measurement is taken after manual addition of reagent and then the integral measured as above. Due to the time it can sometimes take to add converting reagent manually and place the plate/cuvette in the luminometer, it is preferred that the 'B' reading is taken prior to injection of ADP converting reagent, and then a further reading ('C') about 5 minutes after the manual dispensing of the reagent into the well.

4. Skilled persons will appreciate that it is also possible to perform the above manual pippetting embodiment of the assay of the invention without the requirement for decay of the initial ATP signal.

The method of the invention is applicable to prokaryotic and eukaryotic cells. Prokaryotic cells generally require a more intensive ATP-releasing agent due to the presence of a cell wall and to the cell membrane constituents. Suitable such releasing agents for prokaryotic cells include cationic detergents such as benzalkonium chloride, trichloroacetic acid (TCA) and dodecyl trimethylammonium bromide (DTAB). TCA and DTAB inhibit luciferase and would therefore require the sample to be treated with an agent such as cyclodextrin to "neutralise" the releasing agent. For eukaryotic cells, anionic or non-ionic release agents will normally be used, especially polyoxyethylene sorbitan fatty acid esters and polyoxyethylene ethers.

The method of the invention is particularly applicable to animal cell cultures. Examples are given later. It can also be applied to plant cells, e.g. to test citrus tree tissue for contamination by *Spiroplasma citri*, which is responsible for "yellow" disease.

The mycoplasmas to which the present invention applies include *Mycoplasma fermentans, hyorhinis, hominis, pneumoniae, gallisepticum, genitalium, capricolun, mycoides, argini, salivarum* and *orale, Acholeplasma laidlawlii, granularum, florum* and *axanthum, Ureaplasma urealyticum, Thermoplasma acidophilum* and Spiroplasma spp., especially *Spiroplasma citri* and sp. Strain BNRI. Depending on the species, these organisms can infect a wide variety of host cells, both animal and plant.

ATPase activity appears prevalent amongst the world of parasitic microorganisms. Hence, the methods of the present invention can be used to assay a wide range of intracellular and extracellular organisms with ATPase activity.

For intracellular parasites, for example, infection by *Plasmodium falciparum*, red blood cells, or other suitable means of disrupting the host-cell membrane, the common feature is that the host cell will appear essentially healthy and therefore the ATP readings should be similar to an uninfected control cell. If the cells are treated with a Triton-based detergent, or other suitable means of disrupting the host-cell membrane, this will release all the adenylate nucleotides, the ATP results should not deviate significantly from uninfected cells. However, the presence of a parasite with ATPase activity will dramatically increase the levels of ADP. If the cell has an intact membrane and ADP is not being pumped out then there will be little ADP in the culture medium/sample. If the nature of the infection results in ADP being pumped out then there would be ADP present in the culture medium. There could therefore be two measurements done, one prior to lysis and one post disruption of the host cells.

Exemplary intracellular parasites which can be assayed according to the invention include Leishmania, *Trypanosoma cruzi, Trypanosoma brucei, Plasmodium falciparum, Ostertagia leptospicularis, Toxoplasma gondii*, and *Schistosoma mansoni*.

All of the above parasites have been shown to possess ATPase activity. In a still further embodiment of the invention is provided the use of the assay of the invention to determine the efficacy of a drug treatment of the infection. ADP levels should return to normal with eradication of the infecting parasite by the treatment, e.g. a drug.

The releasing agent for releasing intracellular ADP and optionally also ATP, as described above, can be added to the cell sample separately or, more conveniently, along with the bioluminescent reagent.

The bioluminescent reagent can be any of the luciferin/luciferase general type. The active substrate is D-luciferin or a derivative thereof. U.S. Pat. No. 5,374,534 discloses D-luciferin derivatives which may be used with luciferase in the method of the invention. Any other effective derivative (effective to take part in a luminescent reaction with luciferase) can be used. The luciferase enzyme is preferably obtained naturally, especially from fireflies and most especially *Photinus pyralis*. However, the source of the luciferase is not critical, so long as it reacts with luciferin (or a derivative thereof) and ATP to give a detectable signal, e.g. in the bioluminescent reaction. Examples are luciferases from *Luciola cruciata*, Diptera spp. and Coleoptera spp. Of course, ADP and ATP can be measured in other ways, e.g. by high performance liquid chromatography (HPLC), so the invention is not limited to methods involving enzyme reactions.

Synthetic, for example, recombinant luciferase can be used in the invention. It is described by Devine et al., *Biochemica et Biophysica Acta* 1173, No. 2, 121–132 (1993) and in European Patent No 0 301 541 B and U.S. Pat. No. 5,583,024.

Any ADP-converting agent, which converts ADP into ATP, can be used, but preferably this agent comprises the enzyme pyruvate kinase and phosphoenol pyruvate. Other ADP-converting agents can be employed, for example adenylate kinase, glycerol kinase, myokinase and a combination of creatine kinase and creatine phosphate.

Of course, ADP and ATP can be measured in other ways, e.g. by high performance liquid chromatography (HPLC), so the invention is not limited to methods involving enzyme reactions.

Preferred embodiments of the invention will now be described by reference to the following figures and non-limiting examples.

EXAMPLES

Example 1

Reagents
Bioluminescent (Luciferin/Luciferase) Reagent

This was supplied by Labsystems, Helsinki, Finland as a freeze dried powder to be reconstituted prior to use. The powder contains luciferase from *Photinus pyralis* (40 µg), Luciferin (42 µg: believed to contain 96% D-Luciferin; 4% L-Luciferin), bovine serum albumin (50 mg), magnesium sulphate (1.23 mg) and Inorganic pyrophosphate (0.446 µg). It was reconstituted to 10 ml of 0.1 M Tris-acetate buffer, pH 7.75 containing 2 mM EDTA (dipotassium salt).

ATP-releasing Agent 0.1 M Tris acetate buffer pH 7.35 containing 2 mM EDTA (dipotassum salt), 0.25% v/v Triton X-100 and 1 µM dithiothreitol.

ADP-converting Agent

This was prepared by mixing equal volumes of 2 M potassium acetate, 500 units/ml pyruvate kinase (PK) and 100 mM phosphoenol pyruvate (PEP). An equal volume of Tris-acetate buffer pH 7.75 was then added. The PK and PEP were thus diluted 1:6 when the converting reagent was made up from the stock solutions. Since 20 µl of converting reagent is present in 220 µl of the sample and other reagents in the wells, the PK and PEP were further diluted 1:11 in the wells. The concentrations of this reagent in the wells were 30 mM potassium acetate, 7.6 units/ml pyruvate kinase and 1.5 mM phosphoenol pyruvate.

Commercial preparations of pyruvate kinase contain high levels of ATP and ammonium sulphate which is inhibitory to luciferase. Such preparations should be dialysed extensively against a suitable buffer, e.g. Tris-acetate buffer, before use. A glycerol preparation, free of ammonium sulphate, is very useful.

The cell lines tested were cultures of:

K562, Human Chronic Myeloid Leukaemia in blast crisis.

HL-60, Human Acute Promyelocytic Leukaemia.

CEM-7, Human T Lymphoblastic Leukaemia

JURKAT, Human T Lymphoblastic Leukaemia.

U-937, Human histiocytic (a lymphoma cell line with monocytic features)

L-929, Mouse fibroblasts

A549, Human Small Cell Lung Carcinoma

The above cell lines are commercially available from Sigma Biosciences, a division of Sigma Chemical Co., or Sigma-Aldrich Co. Ltd. and/or the European Collection of Cell Cultures, CAMR, Salisbury, Wiltshire, United Kingdom and Clonetics (distributed by BioWhittaker) Wokingham, UK.

Method of Assay

Cell lines or primary cell cultures of interest were cultured for various periods of time. Some were maintained in culture for months and a small sample seeded into fresh culture fluid twice weekly, to maintain stocks.

Adherent cell lines were trypsinised and re-seeded weekly. Culture was in conventional transparent tissue culture microplates or white walled, clear bottomed tissue culture microplates in a suitable cell culture medium (e.g. RPMI 1640 supplemented with Foetal Calf Serum). The cultures were found to be contaminated with Mycoplasma fermentans, except for the Jurkat cells which were found to be contaminated with Mycoplasma hyorhinis (PCR tests). Untreated control cell cultures were also included in the wells of the plate. 100 µl of cell suspension was added to the wells of a microtitre plate. Then 100 µl of the ATP-releasing reagent was added to all the wells of the microtitre plate. The samples were incubated at room temperature for 5 minutes.

The microtitre plate was then loaded into the luminometer which was programmed to automatically add 20 µl of luciferin/luciferase reagent and immediately thereafter to take a measurement of luminescent intensity for each well. 20 µl of ADP-converting reagent was then added to each well and each well read and immediately thereafter the luminescent intensity was read.

The assay differs from apoptosis measurement, in that there is not the associated drop in ATP as cells as undergo programmed cell death, nor is there a drop in the cell number. There is simply a massive increase in the amount of ADP present in the cell culture. The cells appear morphologically normal. The assay is therefore defecting much greater amounts of ADP in the presence of very large amounts of cellular ATP. Table 1 shows the ratios for uncontaminated control cell lines ADP/ATP ratios versus those contaminated with Mycoplasma fermentans. The results are averages over several experiments (number=n).

TABLE 1

| Cell Line | ADP/ATP ratios | |
| --- | --- | --- |
| | Controls | Mycoplasma-contaminated |
| U937 | 0.036 ± 0.0036 (n = 10) | 1.53 ± 0.13 (n = 2) |
| CEM7 | 0.14 ± 0.014 (n = 22) | 1.47 ± 0.55 (n = 7) |
| HL-60 | 0.07 ± 0.007 (n = 12) | 2.34 ± 0.86 (n = 3) |
| K-562 | 0.01 + 0.008 (n = 24) | 1.6 ± 0.5 (n = 2) |
| Jurkat | 0.014 ± 0.008 (n = 4) | 1.0 ± 0.26 (n = 5) |

Cells were confirmed to be mycoplasma-positive by the use of the Stratagene Mycoplasma PCR Primer Set. The PCR-based assay took approximately 1.5 days and was not quantitative. Cells were also cultured onto chamber slides, and cytospins prepared for DAPI staining. The DAPI staining method, while relatively quick to perform, is rather subjective and can be difficult to interpret. However, it appeared to confirm the presence of mycoplasmas.

Example 2

The procedure of Example I was followed.

The cell lines tested were U937, Jurkat, HL60, K562, CEM-7, L-929 and A549 (as in Example 1) plus:

L-929 (freshly thawed) and

BCP-1 (lymphoma cell line)

The DAPI stained cytospins were viewed under fluorescence microscopy, and all cell lines appeared positive. The PCR test showed that all cell lines except Jurkat were positive for *M. fermentans*. The Jurkat cells tested were positive for *M. hyorhinis*. The ADP/ATP ratios appeared to increase at a very early stage of infection.

The L-929 cells held as frozen stock seemed to be the source of the infection, as they were positive in the PCR assay before they had even been set up in culture. On thawing of these cells and culturing them for 48 hours, there was already an increase in the ADP:ATP ratio from around 0.1:1, normally observed in a healthy cell population, to 0.37:1 (average of 2 experiments).

The cells were regularly passaged by trypsinisation during a firer 19 days culture. Measurements were taken when the cells had reached a confluent monolayer in the wells of a 96 well plate, so the cell number should have been approximately the same due to the constant area of the wells. The ATP measurement after 21 days culture was not significantly different those after 48 hours. However, the ADP:ATP ratio had increased by 16 fold to 6.2:1 (average of 2 experiments).

Example 3

This Example demonstrates the effect of heat-treating the culture supernatants at 56° C. for 30 minutes. This would normally inactivate any ATPase activity present as a result of lysing the cells with the nucleotide releasing agent. The cells were incubated at $1 \times 10^5$ ml$^{-1}$ and ATP was measured immediately after removal from the water bath (controls were left at room temperature for 30 minutes) and 10 minutes later. It can be seen that the heat treatment reduced the light signal decay, by inactivating cellular ATPases and other degradative enzymes. ADP would have accumulated in the culture due to the presence of mycoplasma, and, as the ADP is beat stable, it was still detectable.

TABLE 2

| Cell Type | ATP initially | ATP after 10 minutes | ADP | Ratio |
| --- | --- | --- | --- | --- |
| L-929-56° C.-RT | 2612 | 2189 | 16155 | 5.347 |
| | 2693 | 348 | 9603 | 3.437 |
| U937-56° C.-RT | 5619 | 4378 | 32320 | 4.986 |
| | 5244 | 1406 | 9213 | 1.466 |
| Jurkat-56° C.-RT | 9429 | 7242 | 45589 | 4.067 |
| | 9444 | 1265 | 11860 | 1.112 |
| K-562-56° C.-RT | 7186 | 6673 | 34373 | 3.855 |
| | 6512 | 1578 | 10795 | 1.415 |
| Cem-7-56° C.-RT | 7283 | 5752 | 37172 | 4.314 |
| | 7454 | 1106 | 9721 | 1.156 |
| HL-60-56° C.-RT | 7429 | 5803 | 35537 | 4.002 |
| | 7591 | 2239 | 13660 | 1.505 |
| A-549-56° C.-RT | 1698 | 1319 | 11547 | 6.024 |
| | 1693 | 92 | 7158 | 4.174 |

The data in Table 2 above are shown as the means of two separate experiments, one at 56° C. and one at room temperature (RT), performed in triplicate.

The results show that in the presence of mycoplasmas it is possible to detect the ADP without any signal decay being required.

All prior patents and literature herein referred to are herein incorporated by reference to the extent that they are relied on in relation to describing features of the present invention.

What is claimed is:

1. A method of assay for ATPase producing micro-organisms in a sample suspected of contamination or infection by them, which comprises establishing conditions effective to cause a reaction between the ATPase produced by said micro-organisms and ATP to produce ADP and detecting or measuring the reaction; whereby contamination by ATPase-producing micro-organisms is indicated by an increase in the amount of ADP produced in a contaminated sample compared to the amount of ADP produced in an uncontaminated sample.

2. A method according to claim 1, wherein the sample is of biological cells or is an extract therefrom or lysate thereof.

3. A method according to claim 1, wherein the sample is a cell culture.

4. A method according to claim 2, wherein the sample is a cell culture.

5. A method according to claim 4, wherein the culture is grown in the laboratory for research purposes.

6. A method according to claim 2, wherein the culture is of cells which have been infected by a sample of body fluid taken from a patient and suspected of containing ATPase-producing micro-organisms associated with an illness.

7. A method according to claim 1, wherein the ADP produced from the reaction is detected or measured.

8. A method according to claim 7, wherein the ADP produced is converted to ATP, which is then detected or measured.

9. A method according to claim 8, wherein the sample is of biological cells, the micro-organism contaminating or infecting them produces ADP within or in association with the sample cells, the ADP is released from the cells by adding an ADP-releasing agent to the sample and the ADP is converted to ATP by adding an ADP-converting agent to the sample.

10. A method according to claim 9, wherein the ADP-releasing agent also releases ATP from the cells and readings of the intensity of luminescence are taken (1) after release of ADP and ATP from the cells and before adding any ADP-converting reagent and (2) after adding the ADP-converting reagent, whereby an increase in ATP resulting from conversion of the ADP to ATP is detected or measured.

11. A method according to claim 8, wherein the ADP is converted to ATP by adding an agent which comprises (a) a combination of phosphoenol pyruvate and pyruvate kinase, (b) adenylate kinase or (c) myokinase.

12. A method according to claim 9, wherein the ADP is converted to ATP by adding an agent which comprises (a) a combination of phosphoenol pyruvate and pyruvate kinase, (b) adenylate kinase or (c) myokinase.

13. A method according to claim 10, wherein the ADP is converted to ATP by adding an agent which comprises (a) a combination of phosphoenol pyruvate and pyruvate kinase, (b) adenylate kinase or (c) myokinase.

14. A method according to claim 8, wherein the ATP converted from ADP is detected or measured bioluminescently from the reaction of ATP with (a) luciferin and (b) luciferase or an effective derivative thereof in a light-producing reaction.

15. A method according to claim 9, wherein the ATP converted from ADP is detected or measured bioluminescently from the reaction of ATP with (a) luciferin and (b) luciferase or an effective derivative thereof in a light-producing reaction.

16. A method according to claim 10, wherein the ATP converted from ADP is detected or measured bioluminescently from the reaction of ATP with (a) luciferin and (b) luciferase or an effective derivative thereof in a light-producing reaction.

17. A method according to claim 11, wherein the ATP converted from ADP is detected or measured bioluminescently from the reaction of ATP with (a) luciferin and (b) luciferase or an effective derivative thereof in a light-producing reaction.

18. A method according to claim 1, wherein a pre-determined amount of ATP is added to the sample and a parameter selected from the group consisting of (a) the loss of ATP, consumed in the reaction thereof with ATPase, (b) the gain in ADP resulting from reaction of the added ATP with the ATPase and (c) the absolute amount of ATP+ADP present in the sample is detected or measured.

19. A method according to claim 2, wherein a pre-determined amount of ATP is added to the sample and a parameter selected from the group consisting of (a) the loss of ATP, consumed in the reaction thereof with ATPase, (b) the gain in ADP resulting from reaction of the added ATP with the ATPase and (c) the absolute amount of ATP+ADP present in the sample is detected or measured.

20. A method according to claim 3, wherein a pre-determined amount of ATP is added to the sample and a parameter selected from the group consisting of (a) the loss of ATP, consumed in the reaction thereof with ATPase, (b) the gain in ADP resulting from reaction of the added ATP with the ATPase and (c) the absolute amount of ATP+ADP present in the sample is detected or measured.

21. A method according to claim 4, wherein a pre-determined amount of ATP is added to the sample and a parameter selected from the group consisting of (a) the loss of ATP, consumed in the reaction thereof with ATPase, (b) the gain in ADP resulting from reaction of the added AT with the ATPase and (c) the absolute amount of ATP+AD present in the sample is detected or measured.

22. A method according to claim 5, wherein a pre-determined amount of ATP is added to the sample and a parameter selected from the group consisting of (a) the loss of ATP, consumed in the reaction thereof with ATPase, (b) the gain in ADP resulting from reaction of the added ATP with the ATPase and (c) the absolute amount of AT+ADP present in the sample is detected or measured.

23. A method according to one of claims 18–22, wherein ADP is measured by converting it to ATP and measuring the resulting ATP.

24. A method according to claim 23, wherein the parameter is detected or measured bioluminescently from reaction of ATP with (a) luciferin and (b) luciferase or an effective derivative thereof in a light-producing reaction.

25. A method according to claim 1, wherein the ATPase-producing micro-organisms are mycoplasmas.

* * * * *

UNITED STATES PATENT AND TRADEMARK OFFICE
CERTIFICATE OF CORRECTION

PATENT NO. : 6,951,723 B2
DATED : October 4, 2005
INVENTOR(S) : Sharon Patricia Mary Crouch et al.

It is certified that error appears in the above-identified patent and that said Letters Patent is hereby corrected as shown below:

<u>Column 12,</u>
Lines 23 and 31, replace "AT" with -- ATP --.
Line 24, replace "AD" with -- ADP --.

Signed and Sealed this

Ninth Day of May, 2006

JON W. DUDAS
*Director of the United States Patent and Trademark Office*